United States Patent
Birglehner et al.

(10) Patent No.: US 10,292,686 B2
(45) Date of Patent: May 21, 2019

(54) DAMPER FOR MEDICAL ULTRASONIC PROBE

(71) Applicant: General Electric Company, Schenectady, NY (US)

(72) Inventors: Erich Birglehner, Zipf (AT); Thomas Rittenschober, Zipf (AT)

(73) Assignee: General Electric Company, Schenectady, NY (US)

( * ) Notice: Subject to any disclaimer, the term of this patent is extended or adjusted under 35 U.S.C. 154(b) by 156 days.

(21) Appl. No.: 14/143,235

(22) Filed: Dec. 30, 2013

(65) Prior Publication Data

US 2015/0182200 A1 Jul. 2, 2015

(51) Int. Cl.
*A61B 8/00* (2006.01)
*G01S 7/52* (2006.01)
*G10K 11/00* (2006.01)

(52) U.S. Cl.
CPC ............ *A61B 8/546* (2013.01); *A61B 8/4444* (2013.01); *A61B 8/4483* (2013.01); *G10K 11/004* (2013.01); *G01S 7/52079* (2013.01)

(58) Field of Classification Search
CPC ..... A61B 8/546; A61B 8/4444; A61B 8/4483; G10K 11/004; G01S 7/52079
See application file for complete search history.

(56) References Cited

U.S. PATENT DOCUMENTS

| 5,334,181 | A | * | 8/1994 | Rubinsky | A61B 18/02 606/20 |
| 5,560,362 | A | * | 10/1996 | Sliwa, Jr. | A61B 8/546 600/439 |
| 6,126,619 | A | | 10/2000 | Peterson et al. | |
| 7,298,067 | B1 | * | 11/2007 | Kosinski | H03H 9/1071 310/313 R |
| 8,475,375 | B2 | | 7/2013 | Smith et al. | |
| 8,784,321 | B2 | * | 7/2014 | Courtney | A61B 5/0062 600/109 |
| 2007/0253463 | A1 | * | 11/2007 | Perry | A61M 1/369 374/208 |
| 2008/0146924 | A1 | * | 6/2008 | Smith | G01S 7/52017 600/437 |

(Continued)

FOREIGN PATENT DOCUMENTS

JP 2005-098263 A 4/2005
JP 2005-98263 A 4/2005

(Continued)

OTHER PUBLICATIONS

International Search Report and Written Opinion from corresponding PCT Application No. PCT/US2014/050323 dated Nov. 10, 2014; 10 pages.

(Continued)

*Primary Examiner* — Angla M Hoffa
*Assistant Examiner* — Don N Ho

(57) ABSTRACT

A medical ultrasonic probe includes an ultrasonic probe having a probe head and a connector. The connector includes a fluid cooling system comprising a pump configured to pump a cooling fluid between the connector and the probe head. A damper including a housing has a first portion defining a cavity receiving the cooling fluid and a second portion including a gas that is separated from the first portion by a membrane.

3 Claims, 4 Drawing Sheets

(56) References Cited

U.S. PATENT DOCUMENTS

| | | | |
|---|---|---|---|
| 2009/0112098 A1 | 4/2009 | Vaezy et al. | |
| 2010/0201226 A1* | 8/2010 | Bostrom | G01F 23/2962 310/336 |
| 2010/0228162 A1* | 9/2010 | Sliwa | A61N 7/02 601/2 |
| 2012/0071710 A1* | 3/2012 | Gazdzinski | A61B 1/00016 600/101 |
| 2012/0240769 A1* | 9/2012 | Gerner | B01D 19/0005 96/6 |
| 2013/0031963 A1* | 2/2013 | Ritchie, Jr. | G01N 33/2847 73/61.43 |
| 2015/0099978 A1* | 4/2015 | Davidsen | A61B 8/4483 600/459 |

FOREIGN PATENT DOCUMENTS

| | | |
|---|---|---|
| JP | 2006-158411 A | 6/2006 |
| WO | 2013140311 A2 | 9/2013 |

OTHER PUBLICATIONS

Machine Translation and Copy of Notification of Reasons for Refusal issued in connection with corresponding JP Application No. 2016-543589 dated Mar. 27, 2018.

Machine Translation and Decision of Refusal issued in connection with corresponding JP Application No. 2016-543589 dated Aug. 14, 2018.

\* cited by examiner

DAMPER FOR MEDICAL ULTRASONIC PROBE

BACKGROUND

Medical ultrasonic probes may host a plurality of electronics in the probe handle. Thermal management may become a challenge in the presence of electronics with considerable power consumption in the probe handle. In some cases, the heat generated by this power consumption is not sufficiently removed by means of natural convection via the probe surface. In such cases an additional cooling system such as the liquid cooling systems taught in U.S. Pat. No. 8,475,375, incorporated herein by reference in its entirety, may be employed.

SUMMARY

In one embodiment a medical ultrasonic probe includes an ultrasonic probe having a probe head and a connector. The connector includes a fluid cooling system comprising a pump configured to pump a cooling fluid between the connector and the probe head. A damper including a housing has a first portion defining a cavity receiving the cooling fluid and a second portion including a gas that is separated from the first portion by a membrane.

In another embodiment a vibration damper for an ultrasonic probe includes a damper located within a connector of a portable medical ultrasonic probe. The damper forms an interior chamber. An elastomeric membrane is mounted in the chamber separating the chamber into a first compartment having a sealed air compartment and a second compartment having a fluid inlet port and a fluid outlet port for respectively receiving and releasing a cooling fluid.

In another embodiment a process for providing fluid cooling to medical ultrasonic probe includes providing a medical ultrasonic probe having a probe head with a first heat exchanger. The process further includes providing a connector containing a cooling system connected to the medical ultrasonic probe by fluid lines and comprising second heat exchanger; a pump; and a damper which absorbs vibrations induced in a cooling fluid within by the operation of the pump. The process also includes operating the pump to drive the cooling fluid through the damper, the first heat exchanger and the second heat exchanger through the fluid lines.

DETAILED DESCRIPTION

Figure 1:
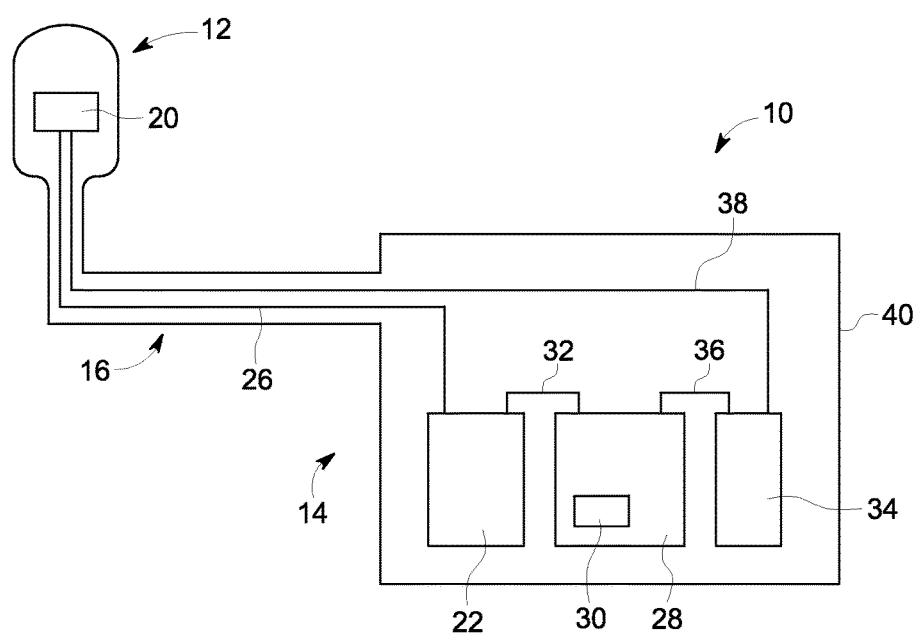
FIG. 1 is a schematic representation of an ultrasound robe and connector.
Figure 5:
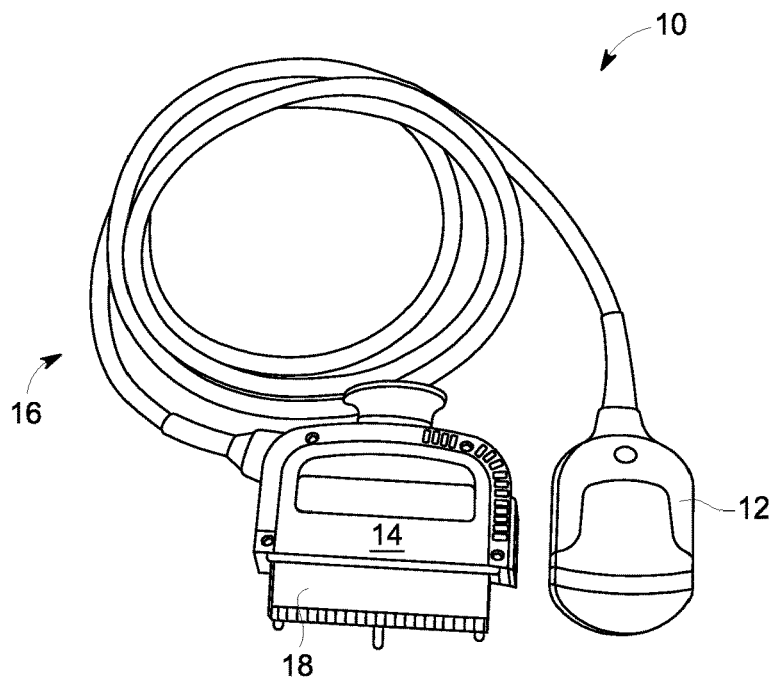
FIG. 5 is a view of an ultrasound probe including a probe head, cable and connector.

Referring to FIG. 1 and FIG. 5, an ultrasound probe 10 includes a probe head 12, a connector 14 and a cable 16 connecting the probe head 12 to the connector 14. Probe head 12 includes a transducer and receiver to send and receive ultrasound energy. Cable 16 provides for electric and fluid communication between the probe head 12 and connector 14. Connector 14 includes an interface 18 to an ultrasound station that may include a monitor and processor for processing the images received from the probe head and sending instructions for operation of the probe head.

Referring to FIG. 1, a cooling system allow for heat created from the ultrasound probe electronics to be removed from the probe. The cooling system includes a first heat exchanger 20 located within probe head 12, a second heat exchanger 22 located within the housing 24. The first heat exchanger 20 is in fluid communication with the second heat exchanger 22 with a conduit portion 26 that extends through cable 16. A cooling fluid is pumped through the conduit portion 26 to transfer heat from the first heat exchanger 20 to the second heat exchanger 24. In one embodiment the cooling fluid is a liquid. A fan (not shown) located within the housing of connector 14 circulates air over the second heat exchanger 22 to remove heat that is transferred from the first heat exchanger 20 to the second heat exchanger 22. In one embodiment second heat exchanger 22 has a number of external ridges or fins to increase the outer surface area of the second heat exchanger 22 to assist in removing heat from the second heat exchanger 22.

Figure 6:
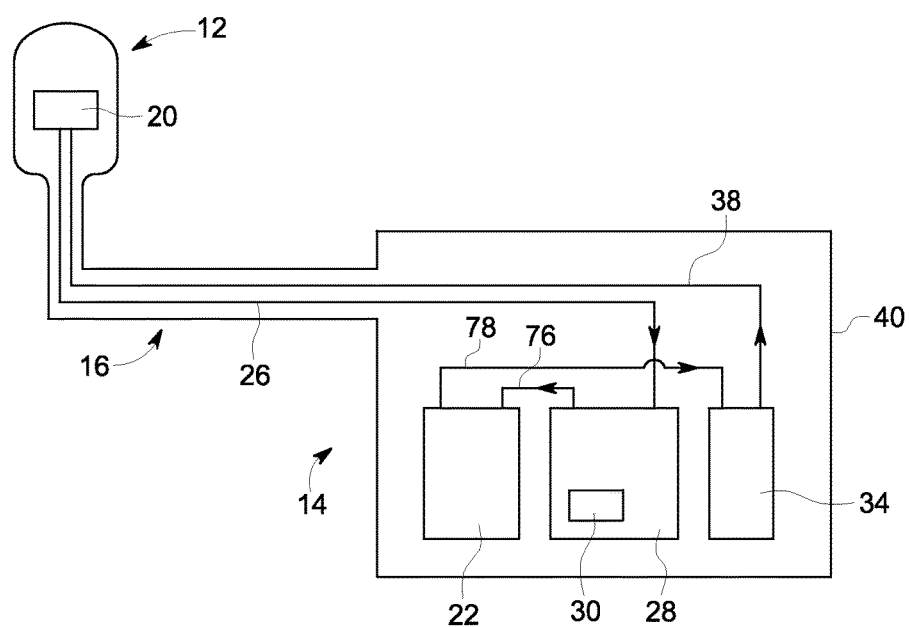
FIG. 6 is a schematic representation of an ultrasound probe and connector with an alternative fluid flow circuit.

In one embodiment, connector 14 includes a reservoir 28 in which a pump 30 is located. Pump 30 is the device that circulates the cooling fluid between the first heat exchanger 20 and the second heat exchanger 24. Second heat exchanger 22 is in fluid communication with reservoir 28 and pump 30 through a conduit portion 32. Pump 30 may cause pressure variations and resultant vibrations in the cooling fluid, as the cooling fluid is circulated between the first heat exchanger 20 and the second heat exchanger 22. In one embodiment, pump 30 also causes the cooling fluid to flow to the first heat exchanger 20 after passing through a damper 34. The cooling fluid is pumped from pump 30 to damper 34 through a conduit 36. The cooling fluid after leaving damper 34 is directed to the first heat exchanger 20 via a conduit 38. Conduit 26, 32, 36 and 38 may be tubes having a hollow portion through which the cooling fluid may circulate. Additionally, other fluid circuits are contemplated. Referring to FIG. 6 the cooling fluid may be directed from the first heat exchanger 20 to the reservoir 28 and/or pump 30 via return conduit 26 and then from the reservoir/pump to the second heat exchanger 22 via a conduit 76 after which the cooling fluid may be circulated to damper 34 via a conduit 78 prior to being returned to the first heat exchanger 20.

In one embodiment, heat exchanger 22, reservoir 28, pump 30 and damper 34 are all located within a housing 40 of connector 14. Damper 34 dampens, suppresses and/or ameliorates the transient and harmonic vibrations that are caused by the cooling fluid induced by pump 30 within the probe head 12. In one embodiment damper 40 is to be understood as a separate element rather than a portion of the conduit or fluid tubes such as a compliant section of a fluid tube on the high-pressure side of the pump. Damper 40 is also to be understood as a deliberate added structure as opposed to the fluid air boundary in a partially filled reservoir. Damper 40 may be secured to or adjacent to an outer surface of reservoir 28 or maybe constructed as part of housing 40.

Figure 2:
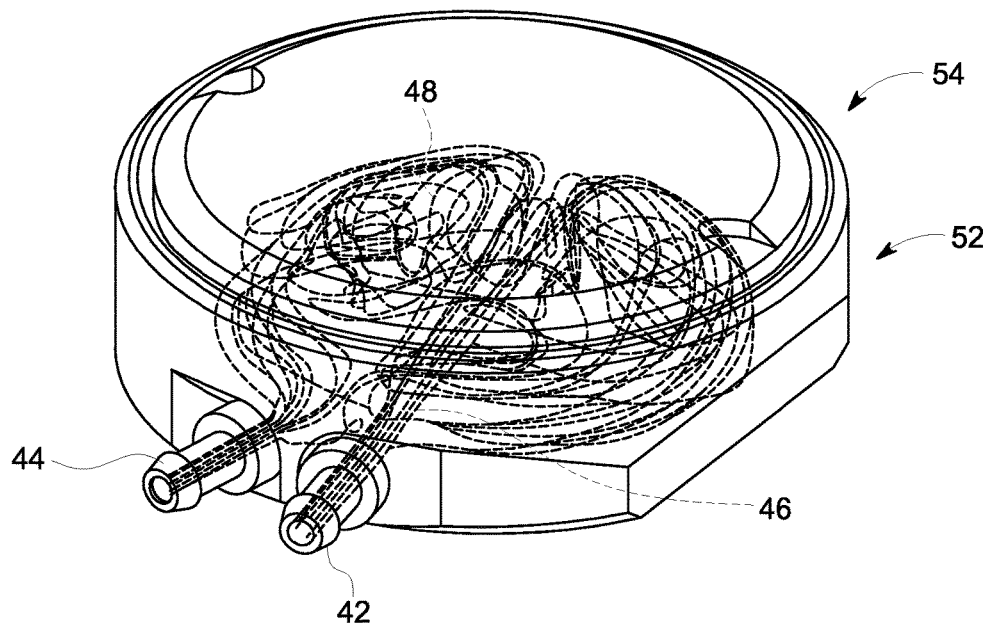
FIG. 2 is representative view of fluid flow within a damper.

Referring to FIG. 2, damper 40 includes an inlet port 42 and an outlet port 44. Inlet port 42 is operatively connected to conduit 36 to allow the cooling fluid from the pump to enter into damper 40. Outlet port 44 is operatively connected to conduit 38 that in turn is connected to first heat exchanger 20. In one embodiment damper 40 is located between the pump and/or reservoir and the probe head 12. This placement reduces and/or eliminates the vibrations within the cooling fluid prior to entering the probe head. It is possible for damper 40 to be placed elsewhere in the cooling fluid flow circuit, such as between the pump and reservoir and or between the second heat exchanger and the pump or between the first heat exchanger and the second heat exchanger.

Referring to FIG. 2, the cooling fluid entering inlet port 42 has a laminar flow. As the cooling fluid circulates within the damper 40 the flow of the cooling fluid is turbulent as represented by the non laminar flow lines 48. The cooling fluid exits damper 40 through second inlet 44 with a laminar flow as the cooling fluid enters conduit 38 and is circulated to first heat exchanger 20.

Figure 3:
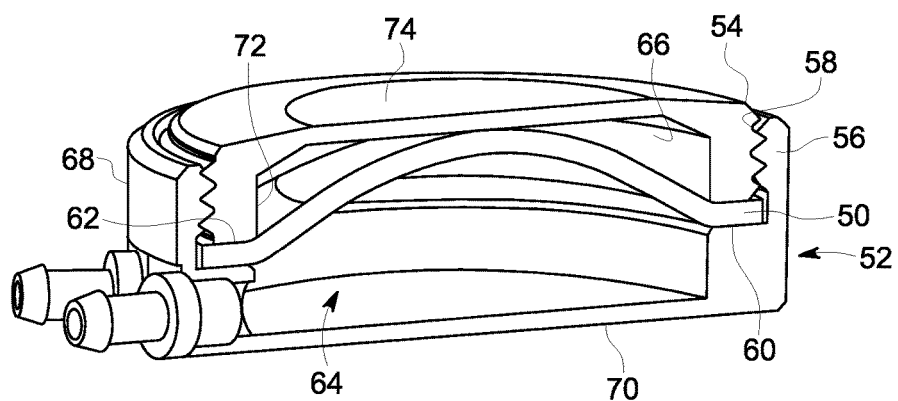
FIG. 3 is a cross-sectional view of the damper.
Figure 4:
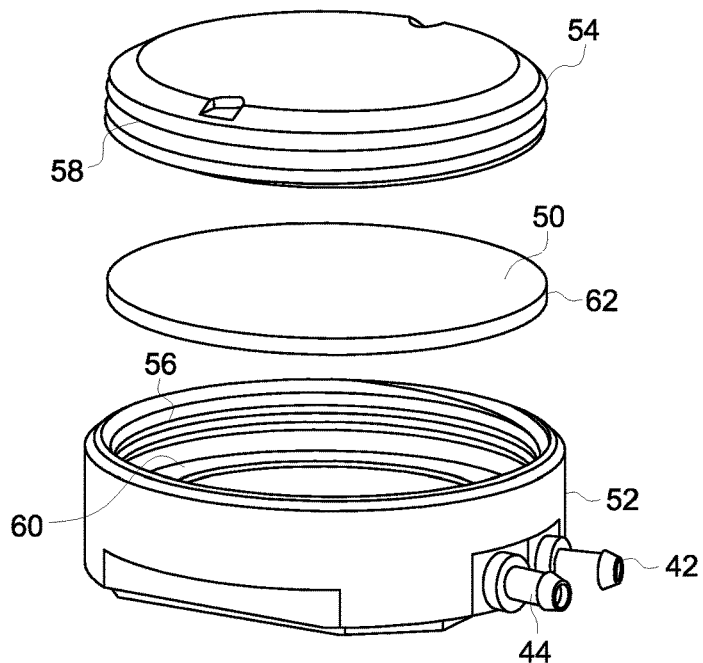
FIG. 4 is an exploded view of the damper.

Referring to FIG. 3 and FIG. 4, damper 40 has a membrane 50, a lower portion 52 and an upper portion 54. The lower portion 52 is provided with inlet port 42 and outlet port 44 that are used for the inlet and outlet of the cooling fluid. The lower portion 52 and the upper portion 54 have mating threads 56 and 58 respectively that engage each other to securely assemble damper 40. The lower member 52 is provided with a ledge 60 that supports the outer circumferential periphery of the membrane 50. When the threads 56 and 58 are fully engaged the peripheral edge of membrane 50 is captured between the ledge 60 and a bottom edge 62 of the upper portion 54 in such a way that a fluid tight hermetic seal is obtained. Cooling fluid introduced into the damper 40 via input port 42 is kept in a cavity 64 formed by the lower portion 52 and the membrane 50.

Membrane 50 may be formed of an elastomeric material such that when it is stretched by pressure variations in the cooling fluid it absorbs energy. The energy of displacing the membrane 50 upward vibrations within the cooling fluid is at least partially dissipated in internal friction inherent in its displacement. In one embodiment the membrane is a fluoropolymer rubber. In one embodiment the membrane is an elastomer with a Shore A hardness of about 75. In one embodiment the membrane has a thickness of about 1 mm. Of course other Shore A hardness values and membrane thicknesses are contemplated.

In one embodiment the upper portion 54 includes male threads that are threaded into the female threads 60 of lower portion 52. Membrane 50 being captured the upper portion 54 and lower portion 52 until significant resistance is met to create a fluid tight seal. In this manner the cooling fluid within cavity 64 does not migrate into the gas cavity 66 between the membrane 50 and upper portion 54.

In one embodiment the lower portion 52 may be formed of a metal such as aluminum. Of course other types of materials are contemplated. Lower portion includes openings through which fluid inlet port 42 and fluid outlet port 44 extend. In one embodiment ledge 60 of lower portion 52 has a width of about 2.5 cm. Cavity 64 is configured such that the cooling fluid has a laminar flow entering inlet port 42 and is converted to turbulent flow as the cooling fluid circulates within the cavity 64 and then is converted back to laminar flow as the cooling fluid exits outlet port 44 through conduit 38. In one embodiment cavity 64 has a cylindrical shape about 20 mm in diameter and about 2.7 mm in height. Of course other diameter and height dimensions are contemplated.

Inlet port 42 and outlet port 44 each have a longitudinal axis that extends through a center portion of inlet port 42 and outlet port 44 respectively. In one embodiment, the longitudinal axis of inlet port 42 is not collinear with the longitudinal axis of outlet port 44. In one embodiment the longitudinal axis of inlet port intersects the longitudinal axis of the outlet port within cavity 64. The arrangement of inlet port 42, outlet port 44 and the geometry of damper 40 contribute to the turbulent flow of the cooing fluid within cavity 64. In one embodiment inlet port 42 and outlet port 44 are closely adjacent and extend from the arcuate outer circumference of the lower portion 52. In one embodiment the longitudinal axis of the inlet port and the longitudinal axis of the outlet port form an angle of about 20 degrees.

The gas within cavity 66 may be air or may be another gas to assist in the removal and minimization of vibrations within the cooling fluid as the cooling fluid is circulated to the probe head 12. Membrane 50 maybe substantially planar in a neutral position or may have an arcuate shape as illustrated in FIG. 3. The shape of membrane 50 may vary depending on the pressure within the cooling fluid circuit and/or the vibrations within the cooling fluid as the cooling fluid enters damper 40.

Lower portion 52 includes an outer arcuate side wall through which the inlet port 42 and outlet port 44 extend and a base floor. Ledge 60 is generally parallel to the plane defined by the base floor. Cavity 64 is defined by the inner surface of the side wall 68 and the inner surface of the base floor 70 as well as the lower or first surface of membrane 50. Similarly, cavity 66 is formed by the inner side wall 72 and the inner side of a cover portion 74 of upper portion 54 and the upper surface or second surface of membrane 50. In one embodiment cavity 66 simply contains the ambient air present when the lower portion 52 and the upper portion 54 are threaded together. In one embodiment cavity 66 is about 3.2 mm high and has a diameter if about 20 mm over most of its height. In one embodiment the upper portion 54 is constructed of a metal such as aluminum. However, other materials are also contemplated.

In one embodiment the longitudinal axis of inlet port 42 and outlet port 44 both lie in a common plane that is parallel to a plane defined by the ledge 60 and or base 70.

In one embodiment the damper is used in conjunction with a Doppler scan used to sense the movement of elements of a human body, such as flowing blood. The damper reduces the probability of artifacts caused by vibrations of the sensing head of probe head 12. In the case of sensing blood flow this reduces or eliminates the possibility of the scan incorrectly indicating reverse blood flow. In one embodiment damper 34 is used with pumps that have a vibrational frequency of around 50 Hz and dominant higher harmonics up to 200 Hz and scans sensing frequencies of greater than 50 Hz.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A medical ultrasonic probe:
an ultrasonic probe having a probe head;
a connector including:
a fluid cooling system comprising:
   a pump configured to pump a cooling fluid between the connector and the probe head; and
   a damper including a housing comprising a first portion and a second portion and a membrane comprising a first surface and a second surface, wherein the membrane is an elastomeric material, where the first portion of the housing and the first surface of the membrane define a first cavity configured to receive the cooling fluid, where the second portion of the housing and the second surface of the membrane define a second cavity configured to contain a gas, where the membrane provides a fluid tight seal separating the cooling fluid in the first cavity from the gas in the second cavity, and where the gas is adapted to remove vibrations in the cooling fluid as the cooling fluid is pumped, wherein the first portion of the housing includes an inlet for receiving the cooling fluid and a separate outlet for the cooling fluid to exit the housing, the inlet and outlet being non-collinear,
wherein the pump pumps the cooling fluid having a laminar flow into the inlet, the first portion causing the flow of the cooling fluid to become turbulent within the first portion, the cooling fluid having a laminar flow as it exits the outlet.

2. A vibration damper for an ultrasonic probe comprising:
a damper located within a connector of a portable medical ultrasonic probe, the damper forming an interior chamber;
an elastomeric membrane mounted in the chamber separating the chamber into a first compartment having a sealed air compartment and a second compartment having a fluid inlet port and a fluid outlet port for respectively receiving and releasing a cooling fluid, where the elastomeric membrane prevents the fluid from contacting the air in the sealed air compartment, wherein the first compartment of the chamber is designed to accept laminar flow cooling fluid at its inlet, cause the flow to become turbulent in the interior of the chamber and then to become laminar again at its outlet, and wherein the membrane and second compartment absorbs vibrations within the cooling fluid as it passes through the first compartment.

3. A process for providing fluid cooling to a medical ultrasonic probe comprising:
providing a medical ultrasonic probe having a probe head with a first heat exchanger;
providing a connector containing a cooling system connected to the medical ultrasonic probe by fluid lines and comprising:
   a second heat exchanger;
   a pump;
   a damper including a housing comprising a first cavity separated from a second cavity by a membrane providing a fluid tight seal between the first cavity and the second cavity, where the damper absorbs vibrations induced in a cooling fluid by the operation of the pump;
operating the pump to drive the cooling fluid through the first cavity of the damper, the first heat exchanger and the second heat exchanger through the fluid lines; and
pumping the cooling fluid with a laminar flow from the pump into the first cavity through a fluid inlet, circulating the cooling fluid within the first cavity in a turbulent flow, absorbing the vibrations in the cooling fluid by the membrane and discharging the cooling fluid in a laminar flow from the first cavity to the first heat exchanger.

* * * * *